United States Patent
Yasuda

(10) Patent No.: US 11,244,200 B2
(45) Date of Patent: Feb. 8, 2022

(54) IMAGE PROCESSING METHOD, IMAGE PROCESSING APPARATUS, AND COMPUTER-READABLE RECORDING MEDIUM HAVING RECORDED THEREON IMAGE PROCESSING PROGRAM

(71) Applicant: SCREEN Holdings Co., Ltd., Kyoto (JP)

(72) Inventor: Takuya Yasuda, Kyoto (JP)

(73) Assignee: SCREEN Holdings Co., Ltd.

( * ) Notice: Subject to any disclaimer, the term of this patent is extended or adjusted under 35 U.S.C. 154(b) by 0 days.

(21) Appl. No.: 16/980,017

(22) PCT Filed: Dec. 21, 2018

(86) PCT No.: PCT/JP2018/047281
§ 371 (c)(1),
(2) Date: Sep. 11, 2020

(87) PCT Pub. No.: WO2019/187420
PCT Pub. Date: Oct. 3, 2019

(65) Prior Publication Data
US 2021/0012151 A1 Jan. 14, 2021

(30) Foreign Application Priority Data

Mar. 26, 2018 (JP) .............................. JP2018-058221
Nov. 15, 2018 (JP) .............................. JP2018-214310

(51) Int. Cl.
*G06K 9/62* (2006.01)
(52) U.S. Cl.
CPC ......... *G06K 9/6215* (2013.01); *G06K 9/6214* (2013.01); *G06K 9/6231* (2013.01)
(58) Field of Classification Search
None
See application file for complete search history.

(56) References Cited

U.S. PATENT DOCUMENTS 5,995,663 A 11/1999 Itsuzaki et al. ............... 382/203
10,521,910 B2 * 12/2019 Wiles .................. G06K 9/00147
(Continued)

FOREIGN PATENT DOCUMENTS

JP 7-210687 A 8/1995
JP 2011-100222 A 5/2011
(Continued)

OTHER PUBLICATIONS

International Search Report dated Mar. 26, 2019 in corresponding PCT International Application No. PCT/JP2018/047281.
(Continued)

*Primary Examiner* — Tahmina N Ansari
(74) *Attorney, Agent, or Firm* — Ostrolenk Faber LLP

(57) ABSTRACT

An image processing method that includes setting a plurality of search areas of a predetermined size having mutually different circumferential positions along a peripheral edge part and extending in a radial direction from a center of a recess toward the peripheral edge part near the peripheral edge part in an image, executing an edge detection in each search area to obtain detected edge position and edge intensity for each search area, obtaining a relative shift amount for making a degree of similarity of image patterns highest for each search area when another search area adjacent to the search area in the circumferential direction is shifted in the radial direction with respect to the search area, and specifying a position of the boundary in one search area based on the edge positions, the edge intensities and the relative shift amounts in the search area and each of the search areas in neighboring ranges in the circumferential direction.

9 Claims, 12 Drawing Sheets

(56) References Cited

U.S. PATENT DOCUMENTS

| | | | |
|---|---|---|---|
| 10,692,216 B2* | 6/2020 | Wiles | C12M 41/46 |
| 2011/0285837 A1 | 11/2011 | Bello et al. | 348/79 |
| 2012/0212748 A1 | 8/2012 | Hollenbeck et al. | 356/614 |
| 2013/0063724 A1 | 3/2013 | Tovey | 356/399 |
| 2013/0315486 A1 | 11/2013 | Franz et al. | 382/190 |
| 2016/0083686 A1* | 3/2016 | Triva | G01N 35/00732 |
| | | | 435/252.1 |
| 2018/0113290 A1* | 4/2018 | Chan | G06K 9/00134 |
| 2019/0234730 A1* | 8/2019 | Hikida | G06T 7/33 |
| 2020/0005466 A1 | 1/2020 | Yasuda | |
| 2021/0012151 A1* | 1/2021 | Yasuda | C12M 1/00 |

FOREIGN PATENT DOCUMENTS

| | | | |
|---|---|---|---|
| JP | 2013-526717 A | 6/2013 | |
| JP | 2014-500955 A | 1/2014 | |
| JP | 5920994 B2 | 5/2016 | |
| JP | 2018-160217 A | 10/2018 | |
| WO | WO 2018/055823 A1 | 3/2018 | |
| WO | WO-2018055823 A1 * | 3/2018 | G06T 7/00 |

OTHER PUBLICATIONS

Written Opinion dated Mar. 26, 2019 in corresponding PCT International Application No. PCT/JP2018/047281.
Extended European Search Report dated Nov. 9, 2021 for counterpart European Application No. 18912506.5.
J.E. Golston et al.: "Boundary detection in skin tumor images: An overall approach and a radial search algorithm", Pattern Recognition., [Online] vol. 23, No. 11, Jan. 29, 1990, pp. 1235-1247, XP055855947, ISSN: 0031-3203, DOI: https://doi.org/10.1016/0031-3203(90)90119-6 Retrieved from the Internet: URL:https://www.sciencedirect.com/science/article/pii/0031320390901196> [retrieved on Oct. 28, 2021] *the whole document*.

* cited by examiner

FIG. 11A

| SEARCH AREA | R0 | R1 | R2 | R3 | R4 | R5 | R6 | R7 |
|---|---|---|---|---|---|---|---|---|
| EDGE POSITION | 5 | 5 | 6 | 5 | — | — | 6 | 5 |
| EDGE INTENNSITY | 5 | 5 | 5 | 5 | 0 | 0 | 2 | 5 |
| RELATIVE SHIFT AMOUNT | 0 | −1 | +1 | 0 | +1 | −1 | 0 | 0 |
| INTEGRATED SHIFT AMOUNT | 0 | 0 | −1 | 0 | 0 | 1 | 0 | 0 |

FIG. 11B (CENTER SIDE) ⟷ (PERIPHERAL EDGE SIDE)

IMAGE PROCESSING METHOD, IMAGE PROCESSING APPARATUS, AND COMPUTER-READABLE RECORDING MEDIUM HAVING RECORDED THEREON IMAGE PROCESSING PROGRAM

CROSS-REFERENCE TO RELATED APPLICATIONS

The present application is a 35 U.S.C. §§ 371 national phase conversion of International Application No. PCT/JP2018/047281, filed Dec. 21, 2018, which claims priority to Japanese Patent Application Nos. 2018-058221 and 2018-214310, filed Mar. 26, 2018 and Nov. 15, 2018, respectively, the contents of all of which are incorporated herein by reference. The PCT International Application was published in the Japanese language.

TECHNICAL FIELD

This invention relates to an image processing technique for specifying a boundary between an invalid area in a peripheral edge part of a recess and a valid area inside the invalid area from an image obtained by imaging a culture medium contained in the recess of a container.

BACKGROUND ART

A container in the form of a flat plate called a well plate or microplate and provided with a plurality of wells (recesses) is used for the analysis of cells. The cells to be analyzed are held together with the culture medium in the wells. Then, the cells are imaged by a camera and subjected to an analysis. If the well and the periphery thereof are imaged at the time of imaging, it is necessary to accurately detect a boundary between the inside of the well, which is a valid area including the cells to be analyzed, and an invalid area in a peripheral edge part from an image.

Concerning this, PTL 1 discloses a method for discriminating a test well wall boundary of a microplate. In the method described in PTL 1, features of the wall boundary of the test well are detected from an image of the microplate. Using the features of the wall boundary, a candidate edge image of the wall boundary is generated. That candidate edge image is analyzed, a spatial position of an outer peripheral boundary of the test well is calculated and an inner peripheral boundary is determined using the calculated information.

CITATION LIST

Patent Literature

[PTL 1] Japanese Patent No. 5920994

SUMMARY OF INVENTION

Technical Problem

A liquid such as a culture liquid is held in the well at the time of imaging. Thus, a concave meniscus is generally formed on a surface of the liquid by surface tension. Further, a side wall surface of the well may be reflected such as when the well side wall surface has a tapered shape or when an imaging direction is inclined. Further, a dark shadow may be produced in the peripheral edge part of the well when an incident direction of illumination light is inclined. Furthermore, air bubbles or substances derived from the cells may adhere to the peripheral edge part of the well.

Due to these reasons, the inner peripheral boundary specified by the method of PTL 1 does not necessarily precisely represent a boundary between a valid area and an invalid area in an image in some cases. Further, due to the same reasons, there are also cases where the boundary becomes partially unclear in the peripheral edge part of the well and cases where a plurality of edges having the features of the boundary are included. Thus, there is a demand for a technique capable of reliably specifying a boundary between a valid area and an invalid area even from such an unclear image.

Solution to Problem

This invention was developed in view of the above problem and an object thereof is to provide a technique capable of reliably and accurately specifying a boundary between an invalid area in a peripheral edge part of a recess and a valid area inside the invalid area from an image obtained by imaging the recess of a container containing a culture medium.

One aspect of this invention is directed to an image processing method for specifying a boundary between an invalid area in a peripheral edge part of a recess and a valid area inside the invalid area from an image obtained by imaging the recess of a container containing a culture medium and, to achieve the above object, the image processing method includes setting a plurality of search areas of a predetermined size having mutually different circumferential positions along the peripheral edge part and extending in a radial direction from a center of the recess toward the peripheral edge part near the peripheral edge part in the image, executing an edge detection in the search areas to obtain detected edge position and edge intensity for each search area, obtaining a relative shift amount for making a degree of similarity of image patterns highest for each search area when another search area adjacent to the search area in the circumferential direction is shifted in the radial direction with respect to the search area, and specifying a position of the boundary in one search area based on the edge positions, the edge intensities and the relative shift amounts in the search area and each of the search areas in neighboring ranges in the circumferential direction.

In the invention thus configured, the plurality of search areas extending in the radial direction are set in the circumferential direction near the peripheral edge part of the recess in the image. The boundary position in the search area is specified based on a result of the edge detected in the radial direction in the search area and the relative shift amount obtained in the circumferential direction.

If a strong edge is detected in the search area, it is said to be highly probable that the edge position thereof is the boundary position, but there is also a possibility of erroneous detection. Further, if the detected edge has a low intensity or a significant edge is not found, compensation by another method is necessary. In this respect, in the invention, a position highly probable to be the boundary position can be specified by the comparison of image contents between the search areas neighboring in the circumferential direction. This can be specifically performed as follows.

Elements in an image causing a boundary to be unclear are thought to be distributed with a certain degree of continuity in a circumferential direction. Accordingly, image contents relatively gently change between a plurality of search areas neighboring each other in the circumferential direction. Thus, the position of the boundary is also thought to gently change. In other words, even in the search area in which a significant edge is not found, if the positions of the boundaries are known in other neighboring search areas, the boundary position can be obtained by estimation from those positions.

A case is considered in which two search areas are relatively shifted in a radial direction and the positions of the both are so aligned that a degree of similarity of image patterns is highest. At this time, image contents are similar in the two search areas and, if the aforementioned continuity is considered, the boundary positions of the both are said to be substantially aligned. Thus, a relative shift amount at this time indicates a change amount of the boundary position between the two search areas. Using this information, the position of the boundary can be estimated from information on the other search areas, regardless of whether or not a clear edge is found in the search area.

In the present invention, the boundary position is specified by combining these pieces of information. Thus, the boundary between the invalid area in the peripheral edge part and the valid area inside the invalid area can be reliably and accurately specified in this invention even if a clear edge is not found near the peripheral edge part.

Advantageous Effects of Invention

As described above, according to the invention, edge detection and a processing of obtaining a relative shift amount making a degree of similarity of image patterns highest between adjacent search areas are performed for each of a plurality of search areas set near a peripheral edge part of a recess. By combining pieces of information obtained in this way, a boundary between an invalid area in the peripheral edge part and a valid area inside the invalid area can be reliably and accurately specified.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF DRAWINGS

FIG. 11A is a first drawing showing a principle of specifying the boundary position from the obtained information.

FIG. 11B is a second drawing showing a principle of specifying the boundary position from the obtained information.

DESCRIPTION OF EMBODIMENTS

Hereinafter, a preferred embodiment of the invention is described with reference to the drawings. In the following description, an "image processing apparatus" of the invention is an imaging apparatus for imaging a well plate which is set to the imaging apparatus. It is described that an "image processing method" of the invention is executed in the imaging apparatus.

Figure 1A:
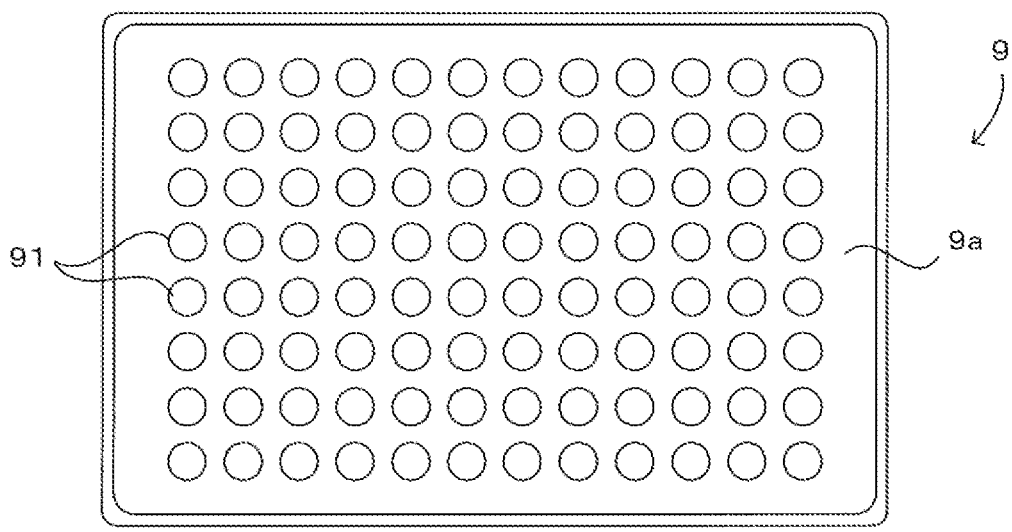
FIG. 1A is a first drawing showing an example of a well plate used in the invention.
Figure 1B:
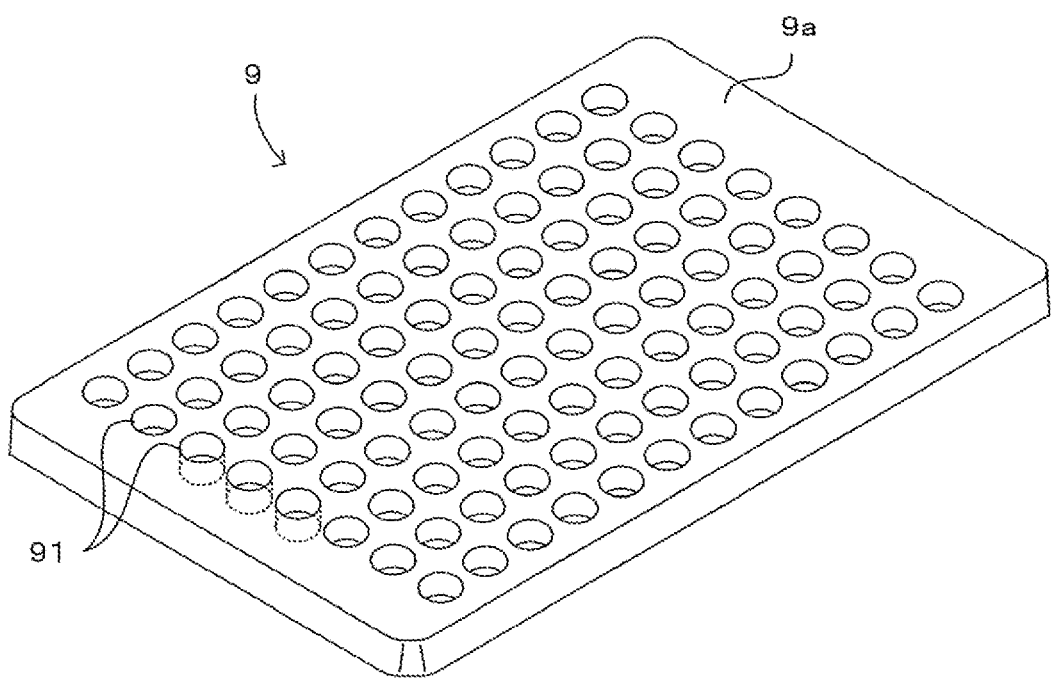
FIG. 1B is a second drawing showing an example of a well plate used in the invention.

FIGS. 1A and 1B are drawings showing an example of a well plate used in the invention. Specifically, FIG. 1A is a top view of a well plate 9 and FIG. 1B is a perspective view of the well plate 9. The well plate 9 is a substantially plate-like specimen container including a plurality of wells 91. A transparent resin which transmits visible light is, for example, used as a material of the well plate 9. The plurality of wells 91 are regularly arranged in the upper surface of the well plate 9. The wells 91 hold a plurality of cells serving as an imaging object together with a culture medium. In this embodiment, the wells 91 are described to have a circular shape in a top view. However, the wells 91 may have another shape such as a rectangular shape or a rounded rectangular shape.

Figure 2:
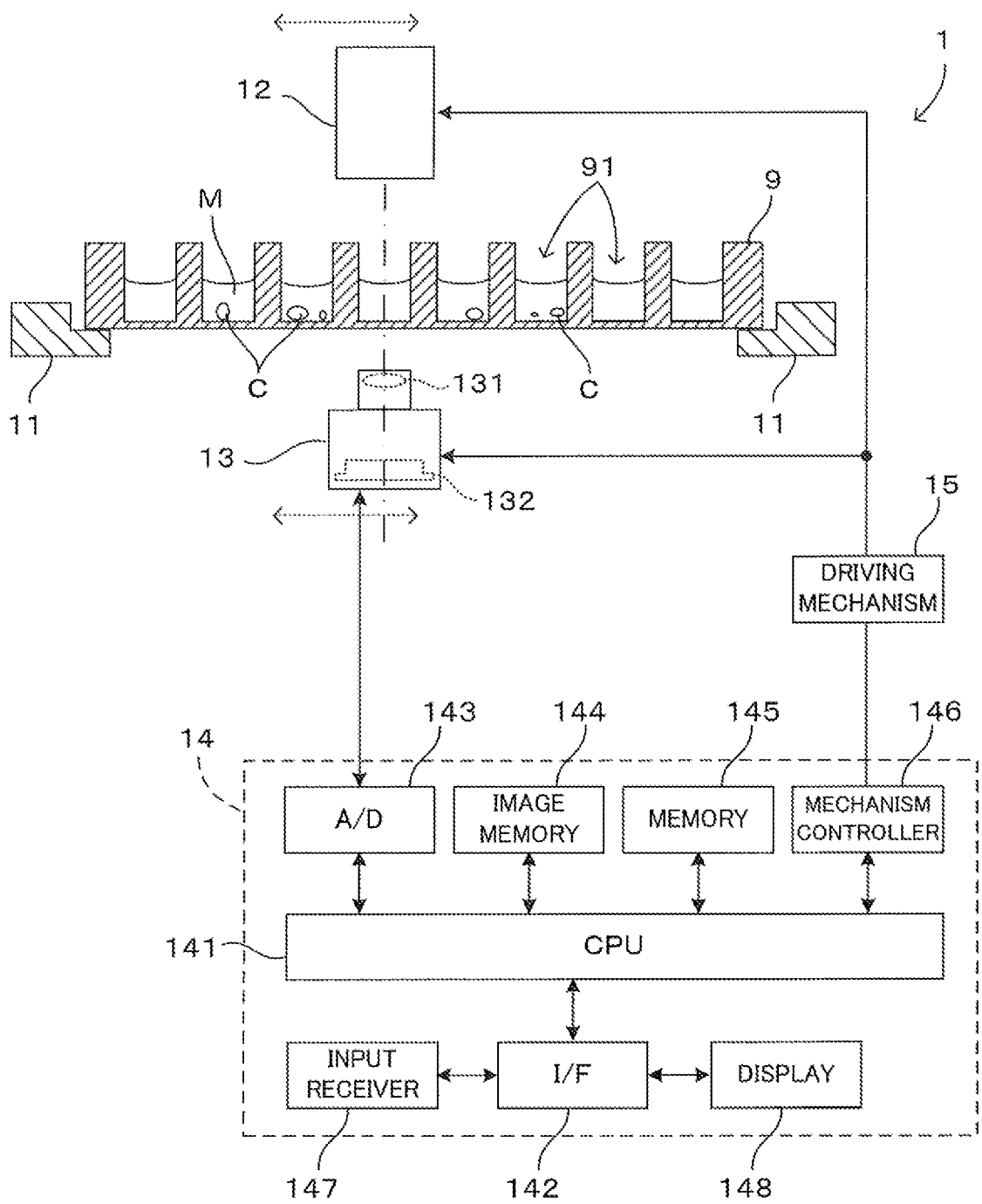
FIG. 2 is a diagram showing a schematic configuration of the imaging apparatus in the embodiment.

FIG. 2 is a diagram showing a schematic configuration of the imaging apparatus in this embodiment. This imaging apparatus 1 is an apparatus for imaging a living specimen such as cells, cell colonies and bacteria (hereinafter, referred to as "cells and the like" and denoted by C) cultured in the culture medium carried in recesses called the wells 91 formed in the upper surface of the well plate 9. Note that the size of the well plate and the number of the wells to be imaged by this imaging apparatus 1 are not limited to these and are arbitrary. For example, well plates having 6 to 384 holes are generally used. Further, this imaging apparatus 1 can be used also in imaging cells and the like cultured, for example, in a flat container called a dish without being limited to use for well plates including a plurality of wells. Here, an XYZ orthogonal coordinate system as shown in FIG. 2 is set to uniformly indicate directions in each figure. For example, an XY plane can be considered as a horizontal plane and a Z axis can be considered as a vertical axis. In the following description, a (−Z) direction is assumed as a vertically downward direction.

A predetermined amount of a liquid serving as a culture medium Mc is injected into each well 91 of the well plate 9, and the cells and the like C cultured under predetermined culture conditions in this liquid become an imaging object of this imaging apparatus 1. The culture medium may be added with an appropriate reagent or may be gelled after being injected in a liquid state into the wells 91. In this imaging apparatus 1, for example, cells and the like C cultured, on the inner bottom surfaces of the wells 91 can be imaged.

The imaging apparatus 1 includes a holder 11 which holds the well plate 9, an illuminator 12 arranged above the holder 11, an imager 13 arranged below the holder 11 and a controller 14 which includes a CPU 141 controlling the operation of these components. The holder 11 holds the well plate 9 in a substantially horizontal posture by being held in contact with a peripheral edge part of the lower surface of the well plate 9 carrying sample together with liquid in each well 91.

The illuminator 12 emits an illumination light toward the well plate 9 held by the holder 11. For example, a white LED (light emitting diode) may be used as a light source of the illumination light. A combination of the light source and an appropriate illumination optical system are used as the illuminator 12. The cells or the like in the well 91 disposed to the well plate 9 are illuminated by the illuminator 12 from above.

The imager 13 is provided below the well plate 9 held by the holder 11. In the imager 13, an imaging optical system is arranged at a position right below the well plate 9. An optical axis of the imaging optical system extends in a vertical direction. FIG. 2 shows a side view. A right and left direction of the figure indicates a horizontal direction and an up and down direction of the figure indicates a vertical direction.

The imaging of the cells or the like in the well 91 is performed by the imager 13. Specifically, light emitted from the illuminator 12 and incident on the surface of the liquid from above the well 91 illuminates the imaging object. Light transmitted downward from the bottom surface of the well 91 is incident to a light receiving surface of an imaging element 132 via the imaging optical system of the imager 13 including an objective lens 131. An image of the imaging object formed on the light receiving surface of the imaging element 132 by the imaging optical system is imaged by the imaging element 132. The imaging element 132 is an area image sensor having a two-dimensional light receiving surface. A CCD sensor or a CMOS sensor can be used as the imaging element 132.

The imager 13 is capable of moving in the horizontal direction and the vertical direction by a mechanism controller 146 provided in the controller 14. Specifically, the mechanism controller 146 moves the imager 13 in the horizontal direction by operating a drive mechanism 15 based on a control command from the CPU 141. By doing so, the imager 13 moves relative to the well 91 in the horizontal direction. Further, focusing is performed by moving the imager 13 in the vertical direction. When the imaging is performed in a state that a whole of the well 91 is included in a field of view, the mechanism controller 146 positions the imager 13 in the horizontal direction such that the optical axis of the imaging optical system coincides with the center of the well 91.

Further, the as indicated by arrows with dotted lines shown in FIG. 2, the driving mechanism 15 moves the illuminator 12 integrally with the imager 13 when the imager 13 is moved in the horizontal direction. Specifically, the illuminator 12 is arranged such that a center of emitted light substantially coincides with the optical axis of the imaging optical system. When the imager 13 moves in the horizontal direction, the illuminator 12 also moves in conjunction with the imager 13. By doing so, whichever well 91 is imaged, the center of the well W and the center of emitted light are always position on the optical axis of the imaging optical system. Consequently, the illuminating condition becomes constant regardless of which well 91 is to be imaged, wherefore imaging conditions can be maintained to be satisfactory.

The image signal output from the imaging element 132 of the imager 13 is send to the controller 14. The image signal is input to an AD converter (A/D) 143 provided in the controller 14 and converted into digital image data. The CPU 141 functions as an image processor which performs appropriate image processings based on the received image data. The controller 14 further includes an image memory 144 for storing image data and a memory 145 for storing programs to be executed by the CPU 141 and data generated by the CPU 141, but these may be integrated. The CPU 141 performs variable calculation processings described later by executing a control program stored in the memory 145.

Besides, the controller 14 is provided with an interface (I/F) 142. The interface 142 has a function of receiving an operation input from a user and presenting information such as processing results to the user. The controller 14 also has a function of performing data exchange with an external apparatus connected via a communication line. To realize the user interface function, an input receiver 147 for receiving an operation input from the user and a display 148 for displaying the messages to the user, a processing result or the like are connected to the interface 142.

Note that the controller 14 may be an exclusive device including above hardware. Further, the controller 14 may be a general-purpose processing device such as a personal computer or a workstation installed with the control program for performing the process described later. Specifically, a general-purpose computer apparatus may be used as the controller 14 of the imaging apparatus 1. When a general-purpose processing device is used as the controller 14, the imaging apparatus 1 may have just a minimal control function for controlling each components of the imager 13 and the like.

Figure 3:
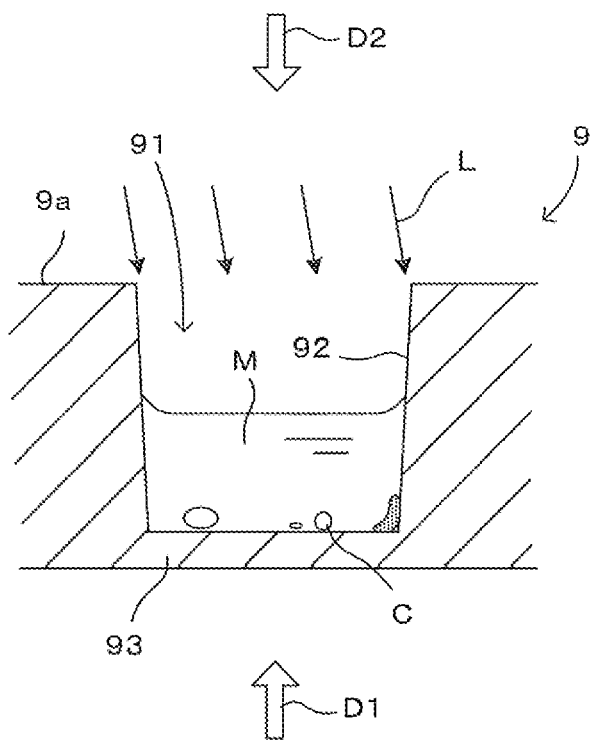
FIG. 3 is a diagram showing a problem in imaging.

FIG. 3 is a diagram showing a problem in imaging. More specifically, FIG. 3 shows a side section of the well 91 containing the culture medium M. As shown in FIG. 3, a side wall surface 92 of the well 91 may be formed into a tapered shape whose cross-sectional area is gradually reduced from a top part toward a bottom part. Further, a protrusion due to a meniscus is produced in a part where the culture medium M injected into the well 91 is in contact with the well side wall surface 92. Further, the shadow of the well side wall surface 92 may be reflected on a liquid surface due to illumination light L incident obliquely to a vertical direction. Furthermore, wastes and the like derived from the cells may adhere to a connecting part of the side wall surface 92 and a bottom surface 93 of the well 91.

When the well 91, which can assume such a state, is imaged from the side of the bottom surface 93 as indicated by an arrow D1 or from an upper opening side as indicated by an arrow D2, a contour may become unclear in the peripheral edge part of the well 91 due to various causes described above.

Figure 4A:
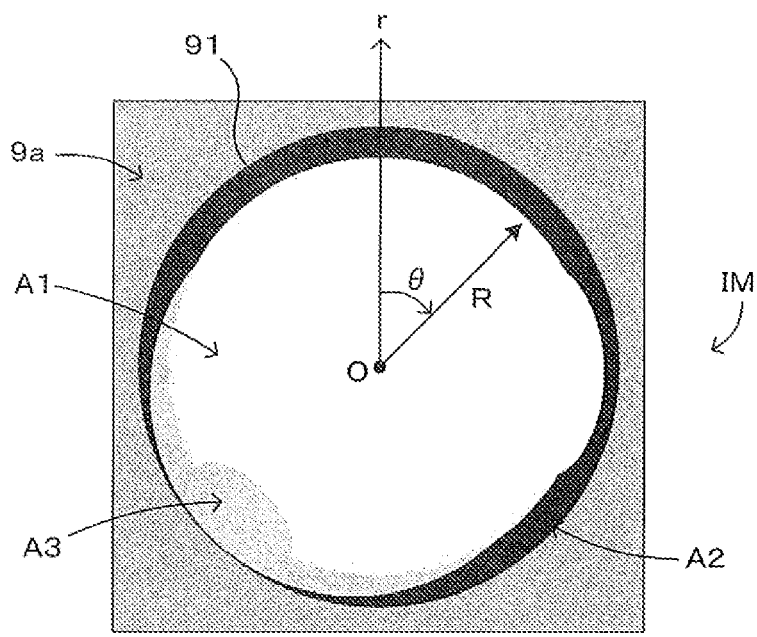
FIG. 4A is a first drawing schematically showing an example of an image obtained by imaging the well.
Figure 4B:
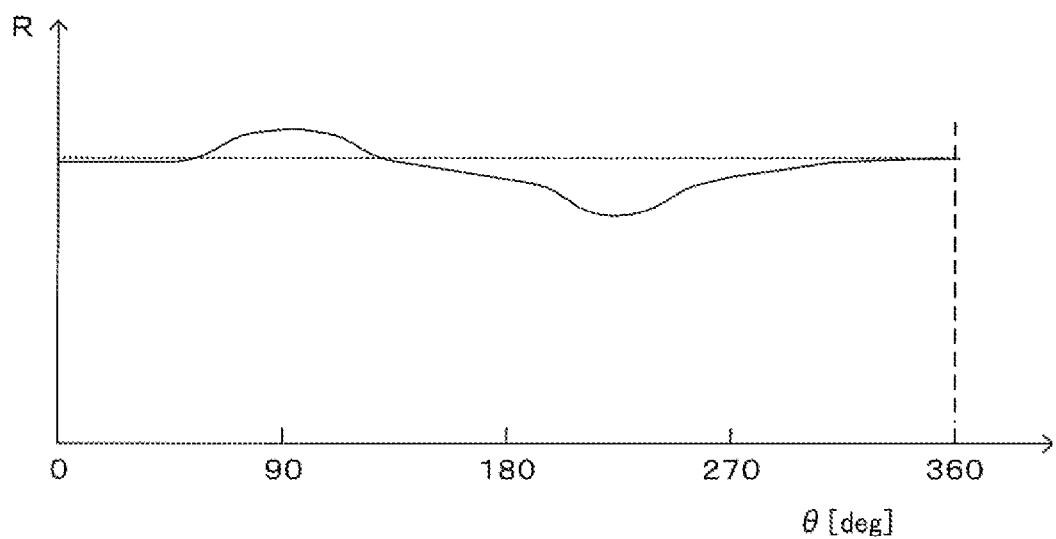
FIG. 4B is a second drawing schematically showing an example of an image obtained by imaging the well.

FIGS. 4A and 4B are drawings schematically showing an example of an image obtained by imaging the well. As shown in FIG. 4A, irregular shading appears, particularly, near the peripheral edge part of the well 91 due to the causes described above in an image IM obtained by imaging the well 91 to include a part of a well plate upper surface 9a. In the image IM, images of the cells to be analyzed and the like are included in a substantially uniform area A1 having a high luminance in a central part. An area A2 reflected darker due to the taper of the well side wall surface, the meniscus and the like and an area A3 having a different luminance from the central part due to substances adhering near the peripheral edge part need to be excluded since these areas may cause an analysis error. Thus, the position of a boundary dividing between the area A1 in the central part and the other areas needs to be specified from the image.

In this specification, the uniform area A1 having a relatively high luminance is referred to as a "valid area" from which images of the cells and the like to be analyzed can be satisfactorily extracted. On the other hand, the areas A2, A3 having irregular shading and unusable for analysis in the well peripheral edge part are referred to as an "invalid area". Then, what is required is to specify the boundary between the valid area and the invalid area from the image.

Here, a point O regarded as a virtual center of the well 91 in the image is set as an origin as shown in FIG. 4A. Then, a polar coordinate system (r, θ) is set with a radial direction from the origin O toward the peripheral edge part serving as a direction of a radius vector r and a rotation direction about the origin O serving as a direction of a deflection angle θ. An upward direction from the origin O in the image can be, for example, set to be θ=0 as a starting point of the deflection angle θ.

A distance from the origin O to the boundary between the valid area A1 and the invalid area in the radius vector direction is expressed by R for various deflection angles θ. Then, as shown in FIG. 4B, the boundary between the valid area A1 and the invalid area can be expressed by a profile obtained by plotting the distance R in relation to the deflection angle θ. In other words, by obtaining this profile, the position of the boundary in the image is specified. An image processing of this embodiment to described next is for obtaining this profile. A basic way of thinking is first described and, thereafter, specific processing contents are described.

Figure 5A:
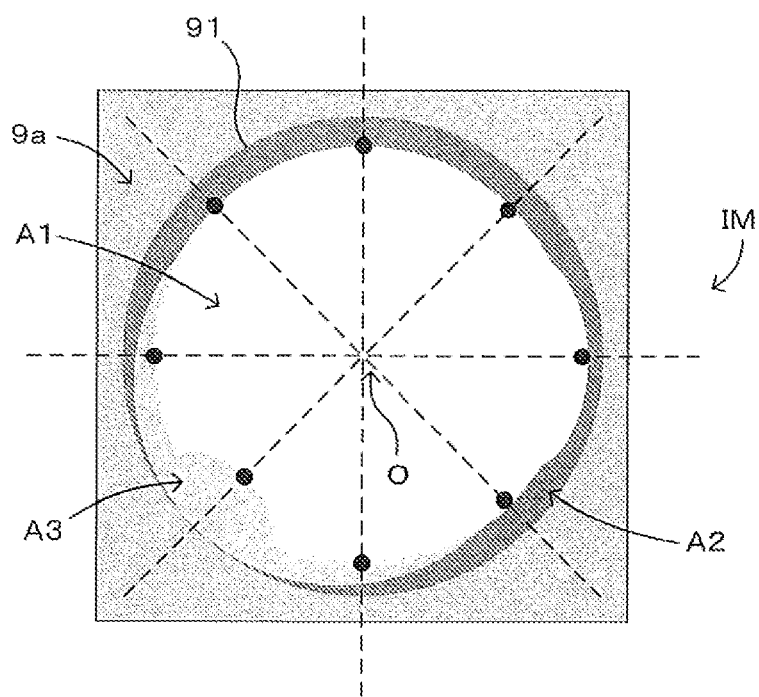
FIG. 5A is a first drawing showing the principle of the image processing in the embodiment.
Figure 5B:
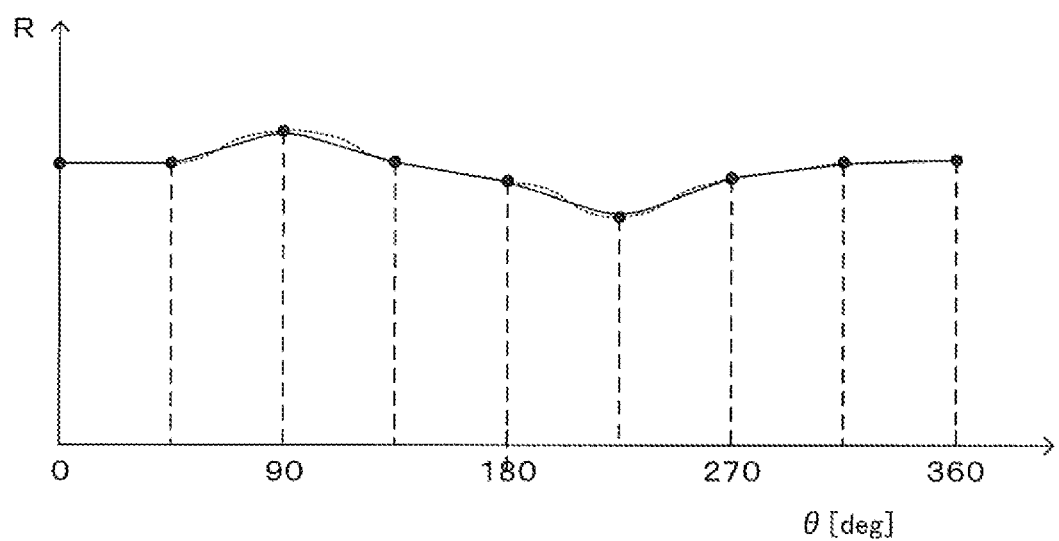
FIG. 5B is a second drawing showing the principle of the image processing in the embodiment.

FIGS. 5A and 5B are drawings showing the principle of the image processing in this embodiment. As shown by broken lines in FIG. 5A, a plurality of radius vector directions radially extending from the origin O can be set. Although eight radius vector directions are set from the origin O at equal angular intervals here, the number of the radius vector directions is arbitrary. As this number increases, boundaries having more complicated shapes can be dealt with, but a time required for the processing becomes longer. Further, the radius vector directions need not necessarily be set at equal angular intervals, but it is advantageous to have such a regularity for the convenience of a computational processing.

The boundary between the valid area A1 and the invalid area is detected on each radius vector set in this way. If the distance R from the origin O at the detected boundary position is plotted in relation to θ and plot points are connected by a smooth curve shown by a solid line as shown in FIG. 5B, a curve close to a target profile represented by a dotted line in the figure is obtained. Therefore, if the position of the boundary can be specified on each radius vector, a necessary profile can be obtained by appropriate curve approximation. Examples of specific processing contents are described below.

Figure 6:
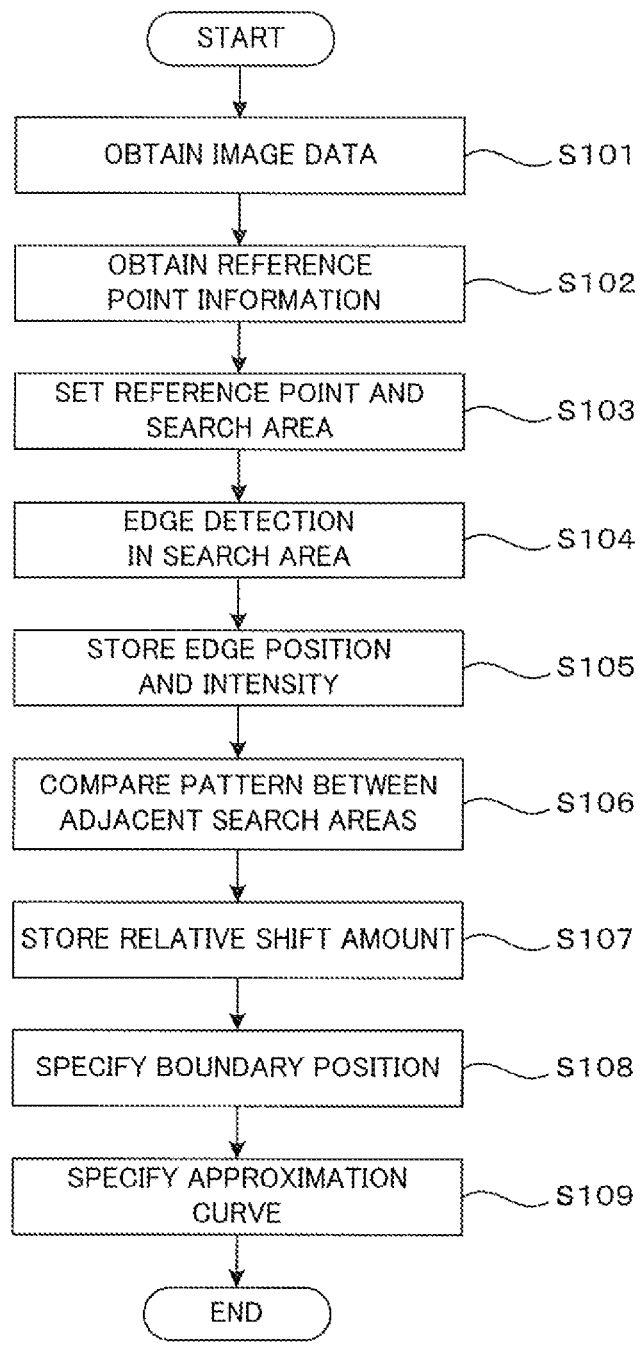
FIG. 6 is a flow chart showing the image processing in the embodiment.

FIG. 6 is a flow chart showing the image processing in this embodiment. This image processing is one embodiment of the "image processing method" according to the invention. This processing is realized by the CPU 141 provided in the controller 14 of the imaging device 1 executing the control program stored in advance in a memory 145 to cause each part of the device to perform a predetermined operation. Note that this processing can be realized also in a computer device having a general configuration if image data is prepared in advance. In that sense, the invention can be realized as a program to be executed by a computer or as a recording medium recording that program.

At first, image data obtained by imaging the well is obtained (Step S101). This imaging device 1 has an imaging function and the image data can be obtained by imaging the well 91 provided in the well plate 9 set in the holder 11. Alternatively, image data given from an external imaging device or a storage device via the interface 142 may be obtained.

Subsequently, reference point information for setting reference points in the image is obtained (Step S102). The reference point information is information for specifying approximate positions of the well peripheral edge part in the image and needs not represent exact positions of the peripheral edge part. For example, the reference point information can be generated in advance, for example, from design data on the opening size and the shape of the well 91 and the like. Such information may be stored in the memory 145 in advance or may be given by an instruction input by a user if necessary. Further, approximate values of a center position, a diameter and the like of the well 91 may be obtained by a simple image processing for the obtained image. Further, a center of the image may be virtually set as a center of the well under the premise that an optical axis at the time of imaging and the well center substantially coincide.

A plurality of reference points are set in the image based on the reference point information given in this way. Together with this, a search area including the reference point is set for each of the reference points (Step S103).

Figure 7A:
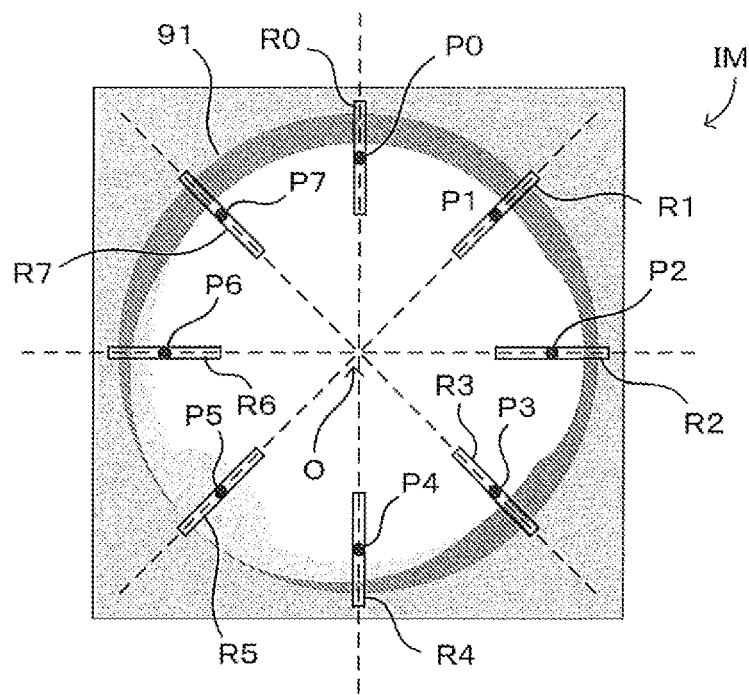
FIG. 7A is a first drawing showing the reference points and the search areas.
Figure 7B:
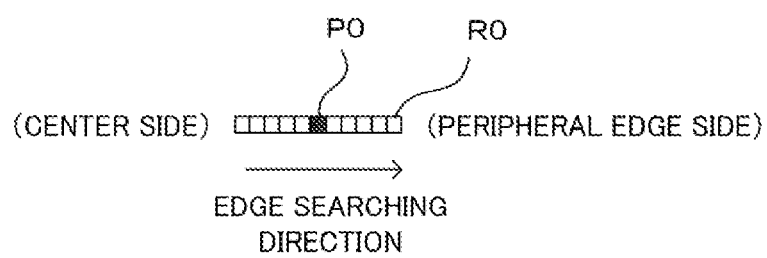
FIG. 7B is a second drawing showing the reference points and the search areas.

FIGS. 7A and 7B are drawings showing the reference points and the search areas. Here, eight reference points P0 to P7 are set about an origin O at equal angular intervals. However, the number and arrangement of the reference points are not limited to these. The plurality of reference points need to be provided at positions different in a circumferential direction near the peripheral edge part of the well 91. The reference points are preferably provided in a dispersed manner in the circumferential direction to accurately specify the boundary position over the entire circumference of the peripheral edge part.

First, the setting of the reference points P0 to P7 is described. As shown by broken lines in FIG. 7A, a plurality of (here, eight) radius vector directions are selected for the origin O temporarily set based on the reference point information. Then, points located near the peripheral edge part of the well 91 on respective radius vectors are set as the reference points P0 to P7. The reference points need not coincide with points of the peripheral edge part of the well 91. To facilitate later computation, the respective reference points P0 to P7 are preferably equidistant from the origin O.

Subsequently, search areas R0 to R7 each including the reference point and extending in the radius vector direction, i.e. radial direction are set on the respective radius vectors. For example, the search area R0 corresponding to the reference point P0 is a line image having a predetermined length in the radial direction with the reference point P0 serving as a center as shown in FIG. 7B. A width of the search area R0 can, for example, correspond to 1 pixel. A length of the search area R0 is set such that the boundary between the valid area A1 and the invalid area in the radius vector direction is included in the search area. Specifically, the position of the reference point P0 and the length of the search area R0 extending from that point may be set such that an expected variation of the boundary position can be reliably covered. The same also applies to the other reference points P1 to P7 and search areas R1 to R7.

Note that the reference points need not necessarily be located in the centers of the search areas. For example, reference points may be set outside an outer peripheral part of the well 91 and search areas may extend in directions toward the origin O from the reference points. Further, since the information of the reference points is not used in later processings, the search areas may be set in the respective radius vector directions without determining the reference points. In this case, distances from the origin O to the respective search areas are desirably equal to each other. Further, the width of the search area is not limited to 1 pixel and may correspond to a plurality of pixels.

Edge detection is performed for each of the search areas R0 to R7 set in this way (Step S104). Then, the position and intensity of an edge at which an image content shows a steep change, are obtained. The edge position and the edge intensity of each search area R0 to R7 are stored in the memory 145 (Step S105).

An algorithm of the edge detection is not particularly limited and a known one can be used. However, it is desirable that clear edges having an edge intensity of a predetermined value or higher are detected, whereas the absence of the edge is detected if there is only a luminance change having a weak edge intensity. Further, in the edge detection in each search area, a search is desirably conducted from a center side toward a peripheral edge side of the well 91 as shown in FIG. 7B.

Figure 8:
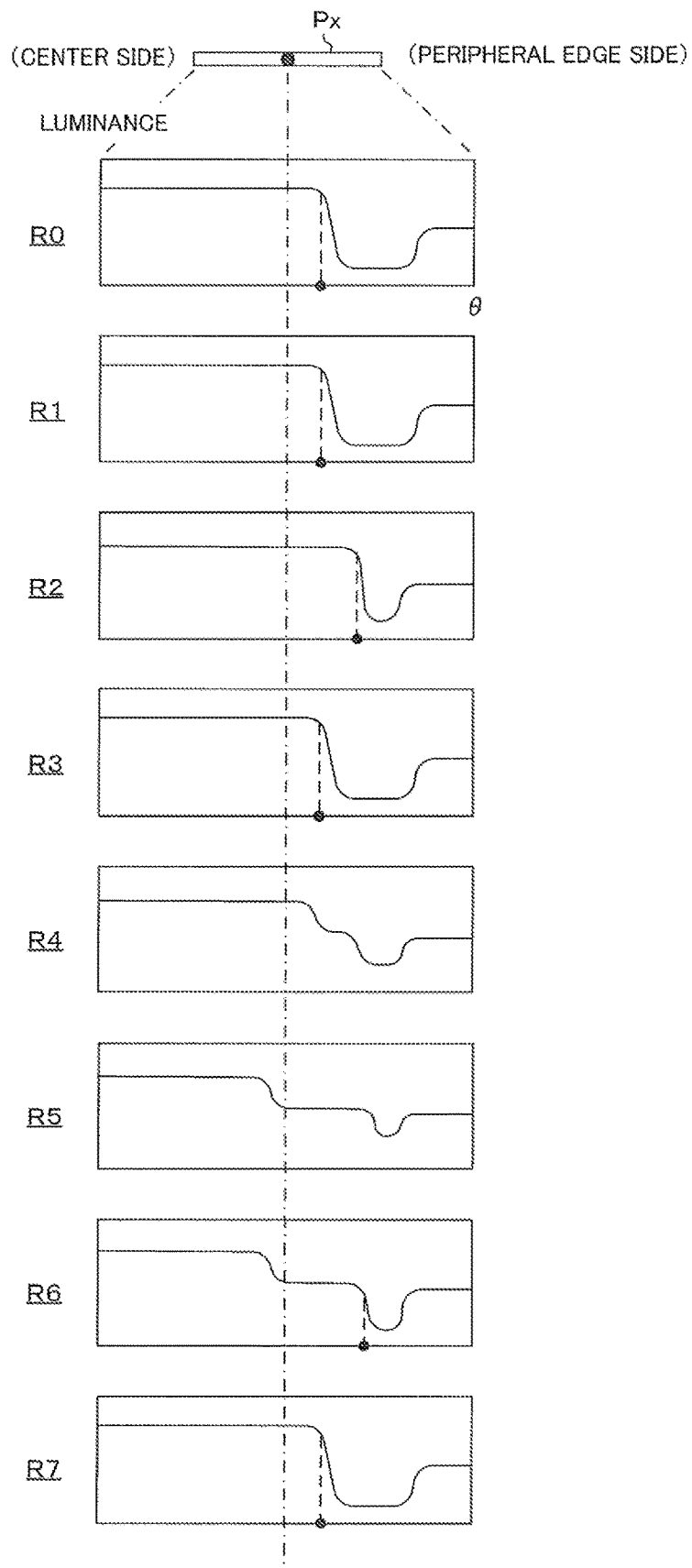
FIG. 8 is a drawing showing examples of luminance changes in the image in the respective search areas.

FIG. 8 is a drawing showing examples of luminance changes in the image in the respective search areas. If the luminance changes from the well center side toward the peripheral edge side are schematically drawn for the respective search areas R0 to R7 set in the image IM illustrated in FIG. 7A, the luminance changes are as in FIG. 8. In any of the areas, a high luminance area corresponding to the luminance of the culture medium M spreads on the well center side (left side in FIG. 8), and a luminance reduction occurs on the peripheral edge side (right side in FIG. 8). A position where the luminance reduction occurs and a luminance change mode varies depending on a state of the well peripheral edge part.

The boundary between the valid area A1 and the invalid area to be obtained partitions between an area in the well central part where the luminance derived from the culture medium M is maintained and an area having a larger luminance variation. Thus, the boundary may be thought to be present at a position where the luminance reduction first occurs when each graph of FIG. 8 is seen from left to right. From this, the edge is searched in the direction from the well central part toward the peripheral edge part. Then, the edge detected first is regarded as valid.

Note that the luminance change mode in the peripheral edge part is possibly a change from a high luminance to a low luminance or a change from a low luminance to a high luminance. If a luminance change direction is known in a specimen as a target, only either one of an edge whose luminance is changing from the high luminance to the low luminance and an edge whose luminance is changing from the low luminance to the high luminance may be detected based on that knowledge.

A black circle attached to a horizontal axis of the graph in FIG. 8 indicates the position of the edge specified by the edge detection. A steep luminance reduction occurs in each of the search areas R0 to R3 and R7 and this position is judged to be an edge. On the other hand, the edge in the search area R6 is an edge having a relatively small luminance change and a weak edge intensity. Further, in the search areas R4, R5 the luminance change is gentle and no edge is detected.

Subsequently, an image pattern in the search area and an image pattern in another search area adjacent to the former search area in the circumferential direction are compared for each search area (Step S106). As shown in FIG. 7A, an image pattern in the well peripheral edge part substantially gently changes in the circumferential direction. Thus, if the intervals between the search areas in the circumferential direction are properly set, differences of the image patterns between the adjacent search areas are not very large. Therefore, the position of the boundary (hereinafter, merely referred to as the "boundary position") between the valid area A1 and the invalid area is thought not to be largely different between the adjacent search areas.

From a property that the image patterns gently change, when the image patterns are compared while one search area is relatively shifted in the radius vector direction with respect to the other search area, a degree of similarity between the image patterns is thought to be highest when the boundary positions are substantially same. In other words, a shift amount when the degree of similarity between the image patterns is highest is said to represent a difference in the boundary position between the both search areas.

Accordingly, if the shift amount when the degree of similarity between the image patterns is highest between the adjacent search areas is obtained, how the boundary position between the both search areas transitions can be grasped. A concept of one-dimensional (or two-dimensional) pattern matching of using one image pattern as a template with respect to the other image pattern can be applied for the degree of similarity. Specifically, the difference of the other image pattern from the one image pattern is obtained for each pixel while the other image pattern is shifted pixel by pixel. A relative shift amount when a total value of absolute values of the differences is smallest represents a change amount of the boundary position between the both search areas. If this relationship is used, another boundary position can be estimated from one boundary position. The relative shift amount obtained in this way is stored in the memory 145 (Step S107). Here, the total value of the absolute values of the differences is used as a scale for evaluating the degree of similarity between the image patterns, and the relative shift amount when this total value is smallest is obtained. However, another known pattern matching technique may be used to evaluate the degree of similarity between the image patterns.

Figure 9A:
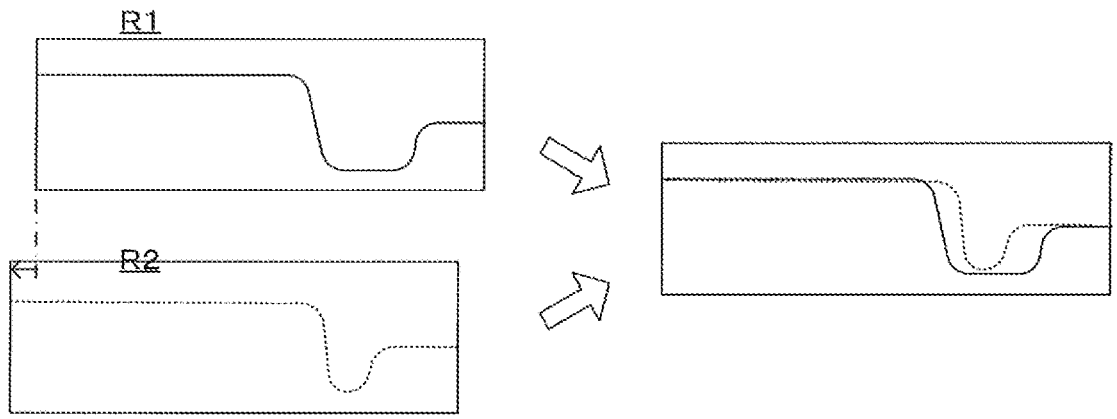
FIG. 9A is a first drawing showing examples of image pattern comparison.
Figure 9B:
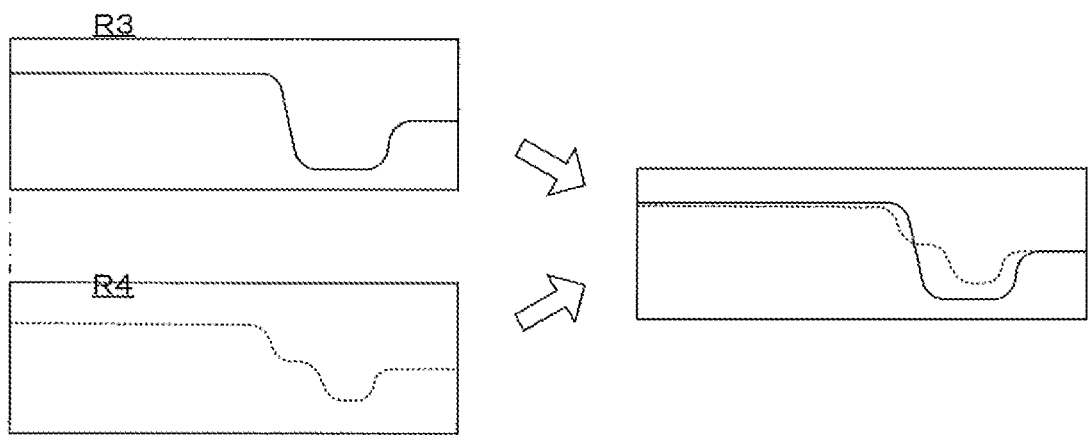
FIG. 9B is a second drawing showing examples of image pattern comparison.
Figure 9C:
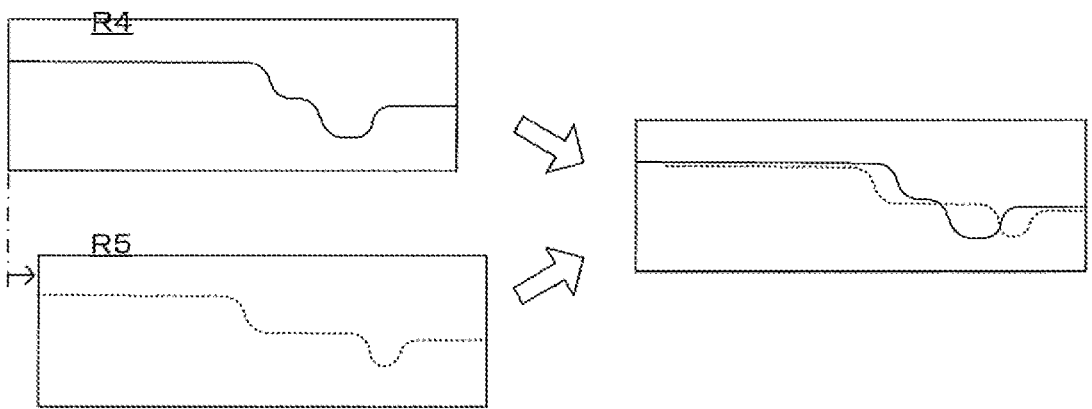
FIG. 9C is a third drawing showing examples of image pattern comparison.

FIGS. 9A to 9C are drawings showing examples of image pattern comparison. FIG. 9A shows a comparison example between two search areas R1 and R2. As can be understood from FIG. 9A, if the both patterns are overlapped with the image pattern of the search area R2 shifted leftward by a certain amount, a difference becomes smaller. This suggests a rightward (i.e. toward the well peripheral edge side) movement of the boundary position in the search area R2 as compared to the search area R1. As shown in FIG. 8, the position of the detected edge also shows a similar tendency and it is said to be highly reasonable to think that this edge position is the boundary position.

Such an estimation of the boundary position by the pattern comparison effectively functions also when the edge was not detected. For example, FIG. 9B shows a comparison example of the search area R3 in which the edge was detected and the search area R4 which is adjacent to the search area R3 in a (+θ) direction and in which no edge was detected. In this case, if the both are overlapped, there is a high correlation even if the shift amount is zero. From this, a movement of the boundary position is thought to be small between the search areas R3 and R4. If the edge position detected in the search area R3 indicates the boundary position, the boundary position in the search area R4 can be estimated to be at the same position.

Further, FIG. 9C shows a comparison example between the search areas R4 and R5, in both of which no edge was detected. Also in this case, if a difference can be minimized, for example, by shifting the pattern of the search area R5 rightward by a certain amount, the shift amount at that time is thought to express a movement amount of the boundary between the both search areas. If the boundary position in the search area R4 can be estimated from the edge position in the adjacent search area R3 as described above, the boundary position of the search area R5 can be further estimated from that.

As just described, the movement amount of the boundary position between the adjacent search areas can be estimated by the pattern comparison between the both search areas, regardless of whether or not clear edges are included. Therefore, the boundary position can be estimated from the boundary position in the surrounding search area also for the search area in which the boundary position is not specified from the edge detection result.

Figure 10:
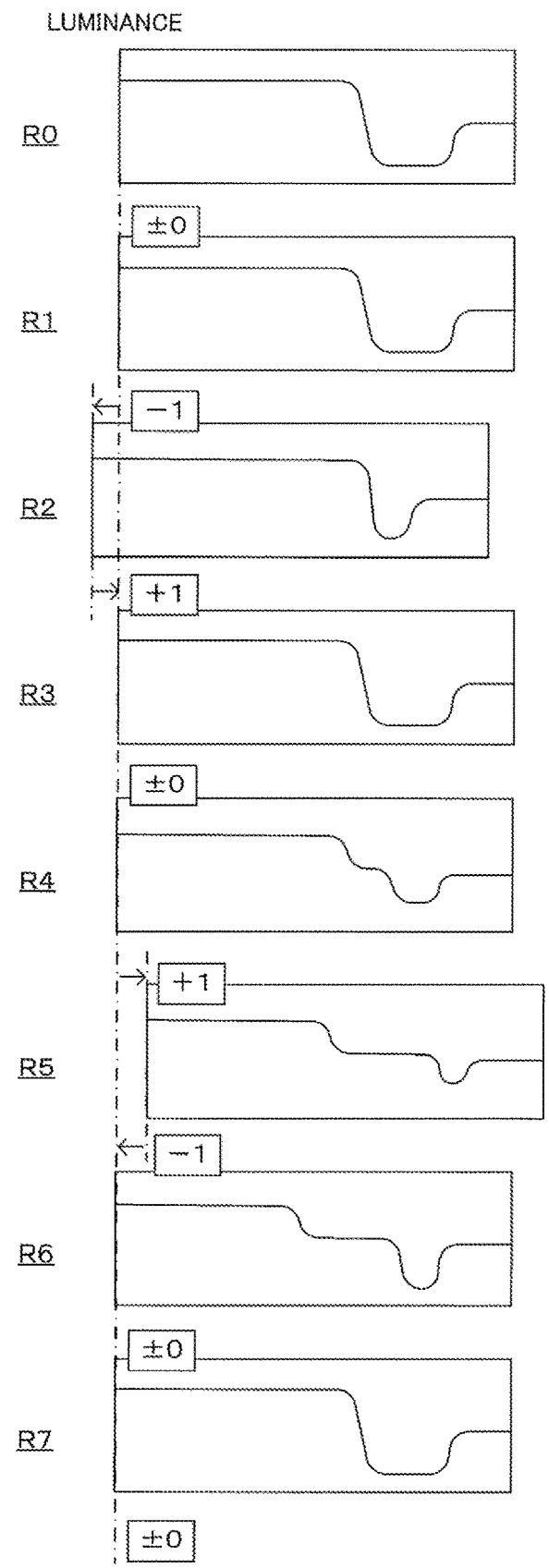
FIG. 10 is a drawing illustrating a result of pattern comparisons between the respective search areas.

FIG. 10 is a drawing illustrating a result of pattern comparisons between the respective search areas. The search area R0 is pattern-compared with the search area R1. Further, the search area R1 is pattern-compared with the search area R2. Similarly, one search area Rx is pattern-compared with another search area R(x+1) adjacent in the (+θ) direction, and a relative shift amount for minimizing a difference between the both is obtained. Here, x is an index indicating the x-th search area. The search area R7 is pattern-compared with the search area R0 adjacent in the (+θ) direction.

In this result, the search area R2 has a leftward relative shift amount of an appropriate 1 unit (e.g. pixel unit) with respect to the search area R1, and the search area R3 has a rightward relative shift amount of 1 unit with respect to the search area R2. For example, if a rightward direction is a positive direction in FIG. 10, it can be expressed that the search area R2 has a (−1) relative shift amount with respect to the search area R1 and the search area R2 has a (+1) relative shift amount with respect to the search area R2. If the relative shift amounts between adjacent ones of the search areas are integrated, a shift amount between the two search areas, which are not adjacent to each other, can be expressed. This is referred to as an "integrated shift amount". The integrated shift amount becomes information indicating a candidate position of the boundary in the circumferential direction.

FIGS. 11A and 11B are drawings showing a principle of specifying the boundary position from the obtained information. By the processings described thus far, the position and intensity of the detected edge, the relative shift amounts from the adjacent search areas and the integrated shift amount obtained as an integrated value of the relative shift amounts are obtained for each of the search areas R0 to R7. These are stored in the memory 145 as shown in FIG. 11A. From these, the boundary positions in the respective search areas R0 to R7 are determined.

A method for obtaining the boundary position from these results is easily understood by graphically showing the table of FIG. 11A as shown in FIG. 11B. Note that each search area R0 to R7 is assumed to have a length of nine pixels to simplify explanation and easily understand the principle. Specifically, the edge positions and the shift amounts shown in FIG. 11A are expressed by a pixel unit. One square expresses one pixel in FIG. 11B.

Bar graph-like diagrams on the left end of FIG. 11B express the image patterns and the detected edge positions of the respective search areas R0 to R7. Each image pattern has shading corresponding to FIG. 7A. Black circles indicate the edge positions. The detected edge intensities are shown to the right of the bar graphs. Further, the integrated shift amounts indicating the transition of the boundary position are expressed by positions on bar graphs to the right of the edge intensities.

If these are successively viewed from top, strong edges are detected in any of the search areas R0 to R3. Further, a change of the detected edge positions coincides with a change of the boundary positions expressed by the integrated shift amounts. From this, it is said to be highly probable that these edge positions express the position of the boundary between the valid area and the invalid area. Therefore, these edge positions can be directly regarded as the boundary positions.

In the next search area R4, there is no large luminance change and no edge is detected. If the integrated shift amount at this time is viewed, it is indicated that the search area R4 has the boundary at the same position as the search area R3 directly above. Thus, at this time, the same position as the boundary position of the search area R3 is regarded as the boundary position of the search area R4. Further, no edge is detected also in the search area R5, but the integrated shift amount indicates that the boundary position of the search area R5 is located at a position one unit to the left of the boundary positions of the neighboring search areas. Therefore, the position suggested by the integrated shift amount is regarded as the boundary position.

In the search area R6, the edge is detected, but the intensity thereof is weaker than the other edges. Further, the edge position thereof also does not coincide with the relationship of the boundary positions between the neighboring search areas indicated by the integrated shift amounts. In this case, the detected edge position is not directly regarded as the boundary position. Specifically, a position determined by the boundary positions in the neighboring search areas, particularly by the boundary position in the search area R7 in which a strong edge is detected, and the integrated shift amount is regarded as the boundary position.

A strong edge is detected in the search area R7. A relationship of the edge position and the edge position in the adjacent search area R0 also coincide with a relationship indicated by the integrated shift amount. Therefore, the edge position can be regarded as the boundary position in this case.

The determined boundary positions are shown on the right end of FIG. 11B. Black circles indicate the boundary positions estimated from the edge detection results. White circles indicate the boundary positions supplemented/corrected in consideration of the results of the pattern comparisons. The boundary positions are set at positions of transition from uniform high-luminance areas on a left side toward to low-luminance areas, and it is understood that a boundary specific purpose shown in FIG. 5A has been achieved.

Thus, by determining the boundary positions of the respective search areas by the above way of thinking, the boundary between the high-luminance area (valid area) on the well center side and the low-luminance area (invalid area) in the peripheral edge part can be accurately specified also for parts in which an edge having a sufficient intensity is not detected.

The principle of the above boundary specification method is summarized as follows.

(1) For the search area in which a strong edge is detected, it is assumed to be highly probable that the edge position indicates the boundary position. Particularly, if a change of the edge position between the neighboring search areas coincides well with a change of the boundary position indicated by the integrated shift amounts, that probability is higher. Further, such a strong edge strongly influences the specification of the boundary positions in the neighboring search areas.

(2) For the search area in which a weak edge is detected and the search area in which no edge is detected, the boundary position is specified with more emphasis placed on a change mode of the boundary positions indicated by the integrated shift amounts. Specifically, the boundary position is estimated from the boundary position(s) determined near this search area based on the change mode of the boundary positions indicated by the integrated shift amounts.

Although not described in detail, such a principle can be realized, for example, by computation based on the following (Equation 1).

$$Pl(x) = \frac{\sum_{k=-m}^{m}\left[\frac{[Pe(M(x+k,n)) - \{Gs(M(x+k,n)) - Gs(x)\}]}{S(M(x+k,n))}\right]}{\sum_{k=-m}^{m} S(M(x+k,n))} \text{ or}$$

$$Pl(x) = \sum_{k=-m}^{m}\frac{\left(\frac{(Pe(M(x+k,n)) - (Gs(M(x+k,n)) - Gs(x)))}{S(M(x+k,n))}\right)}{\sum_{k=-m}^{m} S(M(x+k,n))}$$

In (Equation 1), a variable n represents the number (8 in this example) of the set search areas. A variable x is a parameter for specifying one of the search areas (i.e. x is an integer satisfying a relationship of $0 \leq x < n$). Pl(x) on a left side represents the position of the pixel corresponding to the boundary in the x-th search area Rx and is a solution to be found by this computation. Further, on a right side, Pe(x) represents the edge position detected in the x-th search area Rx and expressed by the pixel position, and S(x) represents the edge intensity.

Further, Gs(x) represents the integrated shift amount of the search area R0 to Rx. Further, a function M(x+k, n) is an abbreviation of a modulo function and precisely expressed by the following (Equation 2):

$$M(x+k,n) = \text{mod}(x+k+n,n) \quad \text{(Equation 2)}.$$

A right side of (Equation 2) is a function of returning a remainder when a value (x+k+n) is divided by a value n.

Further, a variable m is an integer parameter indicating the number of the neighboring search areas to be referred to in specifying the boundary position of one search area Px. Specifically, the variable m indicates how many search areas are regarded as "neighboring" in each of a (−θ) direction and the (+θ) direction for this search area Rx. For example, if m=1, one search area on each of both sides of this search area in the circumferential direction, i.e. the search areas R(x−1), R(x+1), is regarded as a neighboring range. The boundary position in the search area Rx in a center is specified from information obtained for these search areas.

If the parameter m is increased, the information of the search areas distant from one search area is reflected on the boundary position of this one search area. Thus, influences due to noise and erroneous detection can be reduced. On the other hand, there is a problem of canceling out a local variation of the boundary position. If an arrangement interval (this becomes smaller as the parameter n increases) of the search areas in the circumferential direction is sufficiently small, the parameter m can be increased without causing such a problem. From these, the parameters m, n are desirably set according to a degree of luminance irregularity appearing in the well peripheral edge part and how finely the luminance irregularity needs to be detected. Further, since a processing time becomes longer by increasing these parameters, the parameters need to be set also in consideration of this point.

Based on the above principle, the position of the boundary between the valid area and the invalid area is specified for each of the search areas R0 to R7 (Step S108). The obtaining of the boundary positions in this way is equivalent to the specification of the black circle positions shown in FIG. 5A. Accordingly, the boundary between the valid area and the invalid area can be specified over the entire circumference in the circumferential direction by obtaining an approximation curve for interpolating between these boundary positions (Step S109). An approximation method can be appropriately selected from known methods. If a mask is generated, for example, based on the boundary specified in this way, only the valid area A1 can be cut out from the original image.

As described above, in the above embodiment, the well plate 9 corresponds to a "container" of the invention, and the well 91 corresponds to a "recess" of the invention. Further, in the imaging device 1 of the above embodiment, the imager 13 functions as an "image obtaining section" of the invention. Further, the controller 14, particularly the CPU 141, functions as a "control section" of the invention. Note that, in a mode for obtaining original image data from an external device, the interface 142 in charge of communication with the external device functions as the "image obtaining section" of the invention.

Note that the invention is not limited to the above embodiment and various changes other than the aforementioned ones can be made without departing from the gist of the invention. For example, in the above embodiment, an image of the well 91 circular in a plan view is a processing object. However, a rectangular shape with rounded corners, i.e. a so-called rounded rectangular shape, is also widely used as a cross-sectional shape of wells. The image processings of the above embodiment can handle wells having such a shape.

Figure 12A:
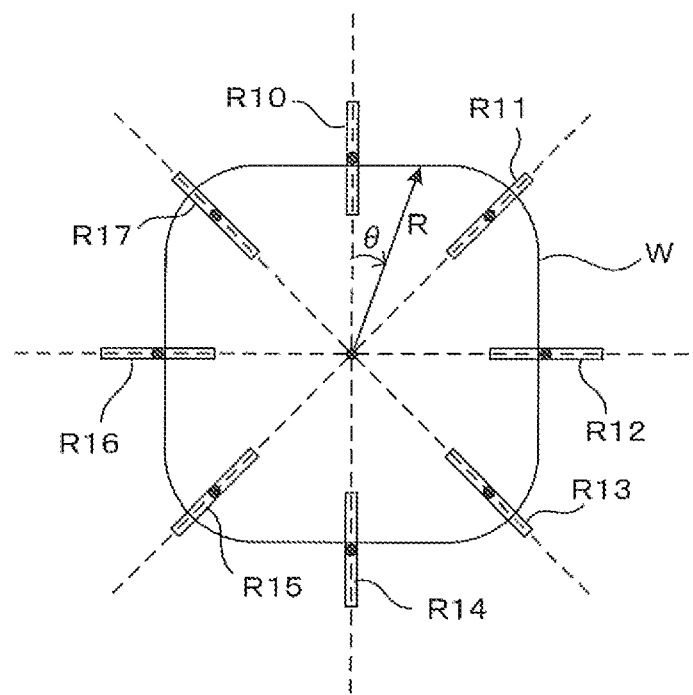
FIG. 12A is a first drawing showing a corresponding example to an image of a rounded rectangular well.
Figure 12B:
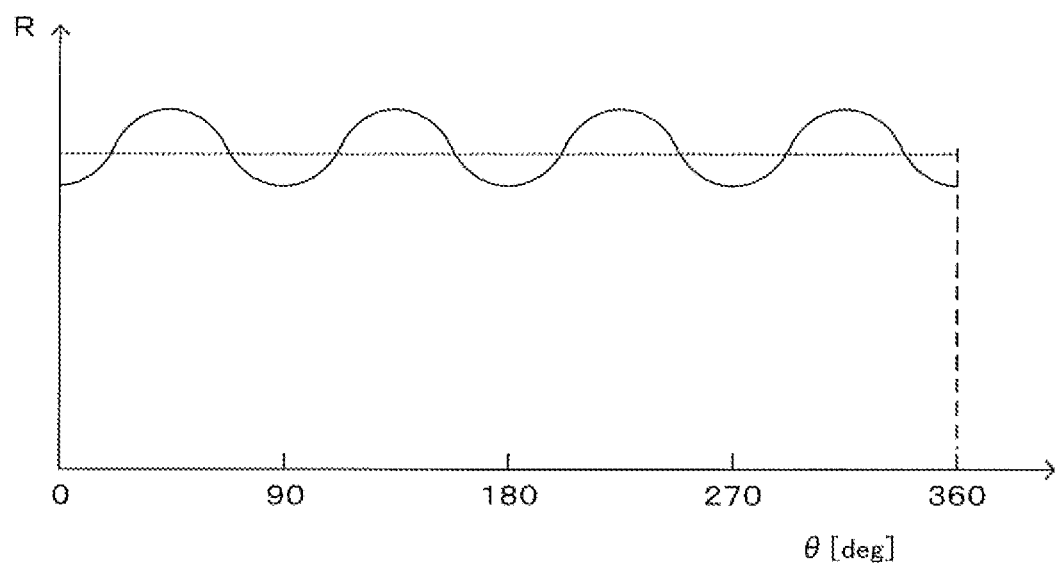
FIG. 12B is a second drawing showing a corresponding example to an image of a rounded rectangular well.

FIGS. 12A and 12B are drawings showing a corresponding example to an image of a rounded rectangular well. As shown by broken lines in FIG. 12A, a plurality of radius vector directions can be radially set from an approximate center also for an image of a well W having a rounded rectangular cross-sectional shape. Search areas R10 to R17 can be set on respective radius vectors and boundary positions in the respective search areas can be specified by a processing similar to the above one.

When the respective search areas are arranged to be equidistant from the center, a distance R from the center to a well peripheral edge part periodically changes even in an ideal state as shown in FIG. 12B. Accordingly, the specified boundary positions also undulate, but the processing itself can be the same as the above one. However, to accurately obtain an approximation curve representing the boundary position over the entire circumference, the number of the search areas is preferably more than in the case of the circular well.

Further, in the above embodiment, luminance values of the respective pixels of the original image are directly used in the original image and the respective search areas. However, the luminance values may be smoothed by appropriate filtering. In this way, erroneous detection due to cell images distributed in the valid area and noise can be reduced. However, attention needs to be paid to a possibility of losing information on fine changes of the boundary position.

Further, calculated values are directly used also, for example, for the detected edge positions and the relative shift amounts. However, smoothing may be performed between the calculated values and the other calculated values adjacent in the radial and circumferential directions. Further, local distortion may be removed by smoothing in the circumferential direction, for example, for the finally specified boundary position.

Further, the edge having a strong edge intensity has a strong influence, out of the neighboring ranges determined by the parameter m, in (Equation 1) of the above embodiment. However, the magnitude of the distance from this search area in the circumferential direction is not reflected. Practically, the influence is thought to be reduced with distance from the search area to be processed. From this, a weight corresponding to a search distance k may be added to (Equation 1).

Further, the relative shift amount for minimizing the image difference between the search areas is obtained, for example, in the pattern comparison of the above embodiment. However, a value of that difference, i.e. information on how much the both images are similar (or deviate) is not used. As the degree of similarity of the images between the adjacent target areas increases, the reliability of the information represented by the relative shift amount is thought to be higher. From this, a weight may be added to the shift amount, for example, according to a matching score in pattern matching.

As the specific embodiment has been illustrated and described above, in the invention, the edge position can be set as the position of the boundary for each search area in which an edge having a larger edge intensity than a predetermined value is detected, whereas the position obtained by correcting the position of the boundary of the other search area adjacent in the circumferential direction according to the relative shift amount of the search area can be set as the position of the boundary of the search area for each search area in which the edge intensity is smaller than the predetermined value or no edge is detected. According to such a configuration, the boundary position can be reliably determined with a high probability also for the search areas in which the edge having a sufficient intensity is not present.

Further, the plurality of search areas can be set to be equidistant from the virtual center set in the central part of the recess. According to such a configuration, differences in distance from the virtual center need not be considered in the comparison of the edge positions and image contents between the respective search areas. Thus, the processing is simplified. This is particularly effective when the recess has a circular shape.

Further, in this case, the plurality of search areas can be provided at equal angular intervals in the circumferential direction. According to such a configuration, differences in circumferential distance of the respective search areas need not be considered in comparing the image contents of the respective search areas in the circumferential direction. In this way, the processing can be simplified as expected.

Further, in the edge detection, the first edge can be detected by searching in the direction from the center toward the peripheral edge part in the search area. In a general case in which a culture medium is injected into a recess, the culture medium is close to transparent, whereas a peripheral edge part is often reflected darker than a central part since light is scattered in various directions in the peripheral edge part. From this, even if there are a plurality of positions corresponding to edges in the search area, the edge between a valid area in a center and an invalid area outside the valid area, out of those edges, can be detected by searching the edges from the central part toward the peripheral edge part. Further, in the edge detection, at least either one of an edge whose luminance is changing from a high luminance to a low luminance and an edge whose luminance is changing from a low luminance to a high luminance may be detected. Particularly, if a luminance change in the direction from the culture medium toward the peripheral edge part is known, the aimed edge can be detected by detecting only either one of a change from the high luminance to the low luminance and a change from the low luminance to the high luminance.

Further, in this invention, a curve approximating a boundary can be specified based on the position of the boundary obtained for each search area. According to such a configuration, information representing the boundary position over the entire circumference in the circumferential direction can be obtained by interpolating between the boundary positions discretely obtained for the respective search areas.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

INDUSTRIAL APPLICABILITY

This invention is for detecting living cells or the like from an image obtained by imaging cells, a cell aggregate or the like. The invention can be particularly suitably applied to medical and biochemical fields such as drug discovery screening.

REFERENCE SIGNS LIST

1 imaging apparatus (image processing apparatus)
9 well plate (container)
13 imager (image obtaining section)
14 controller
91 well (recess)
C cell
M culture medium
R0-R7 search area

The invention claimed is:
1. An image processing method for specifying a boundary between an invalid area in a peripheral edge part of a recess and a valid area inside the invalid area from an image obtained by imaging the recess of a container containing a culture medium, the image processing method comprising:
setting a plurality of search areas of a predetermined size having mutually different circumferential positions along the peripheral edge part and extending in a radial direction from a center of the recess toward the peripheral edge part near the peripheral edge part in the image;

executing an edge detection in each search area to obtain detected edge position and edge intensity for each search area;

obtaining a relative shift amount for making a degree of similarity of image patterns highest for each search area when another search area adjacent to the search area in the circumferential direction is shifted in the radial direction with respect to the search area; and specifying a position of the boundary in one search area based on the edge positions, the edge intensities and the relative shift amounts in the search area and each of the search areas in neighboring ranges in the circumferential direction.

2. The image processing method according to claim 1, wherein the edge position is set as the position of the boundary for each search area in which an edge having a larger edge intensity than a predetermined value is detected, whereas the position obtained by correcting the position of the boundary of the other search area adjacent in the circumferential direction according to the relative shift amount of the search area is set as the position of the boundary of the search area for each search area in which the edge intensity is smaller than the predetermined value or no edge is detected.

3. The image processing method according to claim 1, wherein the plurality of search areas are equidistant from a virtual center set in the central part of the recess.

4. The image processing method according to claim 3, wherein the plurality of search areas are provided at equal angular intervals in the circumferential direction.

5. The image processing method according to claim 1, wherein in the edge detection, a first edge is detected by searching in the direction from the center toward the peripheral edge part in the search area.

6. The image processing method according to claim 1, wherein in the edge detection, at least either one of an edge whose luminance is changing from a high luminance to a low luminance and an edge whose luminance is changing from a low luminance to a high luminance is detected.

7. The image processing method according to claim 1, wherein a curve approximating a boundary is specified based on the position of the boundary obtained for each search area.

8. A non-transitory computer-readable recording medium having recorded thereon a program for performing the image processing method according to claim 1.

9. An image processing apparatus, comprising:

an image obtaining section which obtains an image obtained by imaging a recess of a container containing a culture medium; and a control section which executes the image processing method according to claim 1 upon the image obtained by the image obtaining section.

* * * * *